(12) United States Patent
Chen et al.

(10) Patent No.: US 9,209,413 B1
(45) Date of Patent: Dec. 8, 2015

(54) SPIRALLY CONFIGURED CIS-STILBENE/FLUORENE HYBRID MATERIALS AS HOLE-BLOCKING TYPE ELECTRON-TRANSPORTERS FOR OLED

(71) Applicant: National Tsing Hua University, Hsinchu (TW)

(72) Inventors: Chien-Tien Chen, Hsinchu (TW); Jwo-Huei Jou, Hsinchu (TW)

(73) Assignee: NICHEM FINE TECHNOLOGY CO. LTD. (TW)

( * ) Notice: Subject to any disclaimer, the term of this patent is extended or adjusted under 35 U.S.C. 154(b) by 0 days.

(21) Appl. No.: 14/583,619

(22) Filed: Dec. 27, 2014

(30) Foreign Application Priority Data

Oct. 15, 2014 (TW) .............................. 103135653 A

(51) Int. Cl.
| | | |
|---|---|---|
| *H01L 51/00* | (2006.01) | |
| *C07D 235/20* | (2006.01) | |
| *C07F 9/50* | (2006.01) | |
| *C07D 213/38* | (2006.01) | |
| *C07D 239/26* | (2006.01) | |

(52) U.S. Cl.
CPC .......... *H01L 51/0072* (2013.01); *C07D 213/38* (2013.01); *C07D 235/20* (2013.01); *C07D 239/26* (2013.01); *C07F 9/5027* (2013.01)

(58) Field of Classification Search
CPC .................................................. H01L 51/0072
USPC .......................................................... 544/296
See application file for complete search history.

(56) References Cited

FOREIGN PATENT DOCUMENTS

JP 2010024149 * 2/2010

OTHER PUBLICATIONS

King, Med. Chem., Principle and Practice (1994), pp. 206-208.*

* cited by examiner

*Primary Examiner* — Taofiq A Solola

(57) ABSTRACT

The present invention provides a series of spirally configured cis-stilbene/fluorene hybrid materials, which are spirally-configured cis-stilbene/fluorene derivatives having glass transition temperatures ranged from 110° C. to 135° C., decomposition temperatures ranged from 380° C. to 425° C., reversible electron transport property, and balanced charges motilities. In addition, a variety of experimental data have proved that this spirally configured cis-stilbene/fluorene hybrid materials can indeed be used as a hole-blocking type electron-transporter and/or a host material for phosphorescent OLEDs. Moreover, the experiment data also reveal that the OLEDs using the spirally configured cis-stilbene/fluorene hybrid materials can indeed be used as the hole-blocking type electron-transporter or as a host materials, which are able to show excellent external quantum efficiency ($\eta_{ext}$), current efficiency ($\eta_c$), power efficiency ($\eta_p$), maximum luminance ($L_{max}$), and device lifetime performances much better than the conventional or commercial OLEDs.

1 Claim, 1 Drawing Sheet

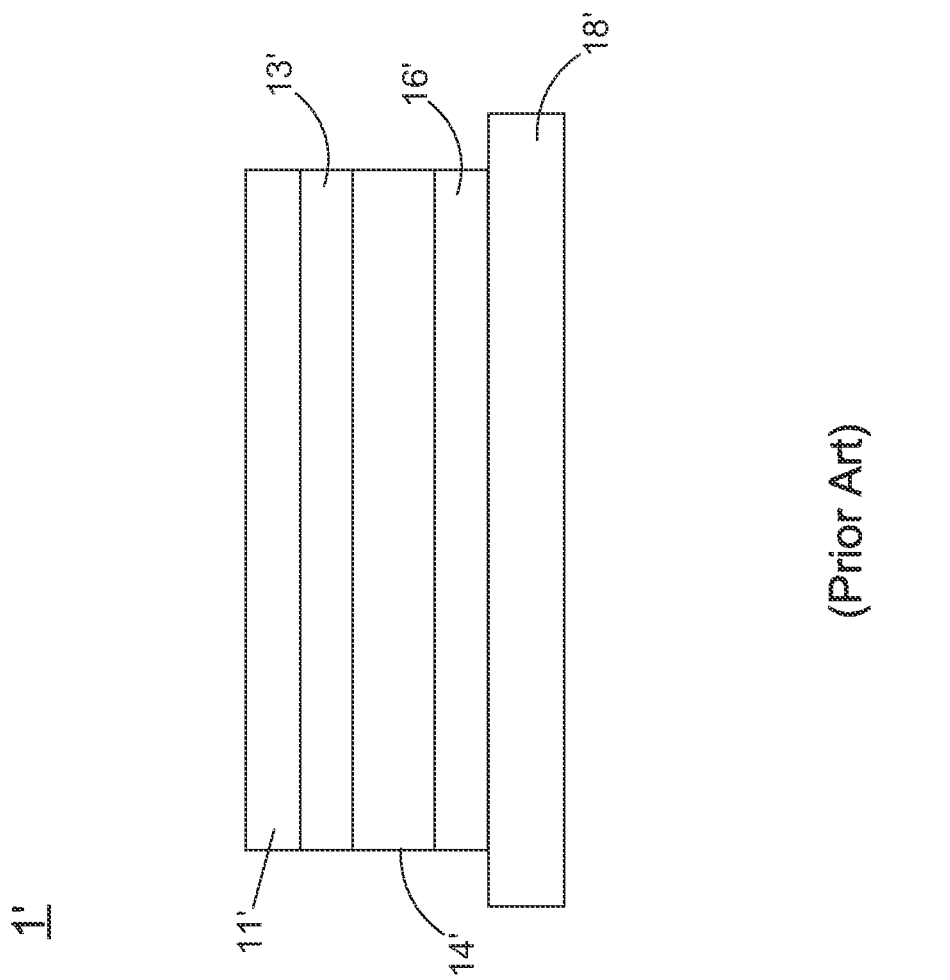

SPIRALLY CONFIGURED CIS-STILBENE/FLUORENE HYBRID MATERIALS AS HOLE-BLOCKING TYPE ELECTRON-TRANSPORTERS FOR OLED

BACKGROUND OF THE INVENTION

1. Field of the Invention

The present invention relates to the technology field of carrier transport materials, and more particularly to a spirally configured cis-stilbene/fluorene hybrid material as a hole-blocking type electron-transporters for OLEDs.

2. Description of the Prior Art

It is well known that organic light emitting diode (OLED) was initially invented and proposed by Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device currently becomes a new generation lighting device or display because of high brightness, fast response speed, light weight, compactness, true color, no difference in viewing angles, without using any LCD backlight plates, and low power consumption.

Recently, some interlayers such as electron transport layer and hole transport layer are added between the cathode and the anode for increasing the current efficiency and power efficiency of the OLEDs. For example, an organic light emitting diode (OLED) 1' shown as FIG. 1 is designed to consist of: a cathode 11', an electron injection layer 13', a light emitting layer 14', a hole transport layer 16', and an anode 18'.

In device function concept, the light emitted by the OLED 1' is resulted from excitons produced by the recombination of electrons and holes in the light emitting layer 14'. However, according to theoretical speculation, the ratio of the excitons with singlet excited state and the excitons with triplet excited state is 3:1. So that, when a small molecular fluorescent material is used as the light-emitting layer 14' of the OLED 1', there are about 25% excitons being used in emitting light, and the rest of 75% excitons with triplet excited state are lost through non-luminescence mechanism. For this reason, the general fluorescent material performs a maximum quantum yield of 25% in limit which amounts to an external quantum efficiency of 5% in the device.

Moreover, researches further find that certain hole transport material can simultaneously perform electron confining ability, such as the material represented by following chemical formulas 1' and 2'. The chemical formula 1' represents the chemical structure of Tris(4-carbazoyl-9-ylphenyl)amine, which is called TCTA in abbreviation. The chemical formula 2' represents the chemical structure of N,N'-Di(1-naphthyl)-N,N'-diphenyl-(1,1'-biphenyl)-4,4'-diamine called NPB in abbreviation.

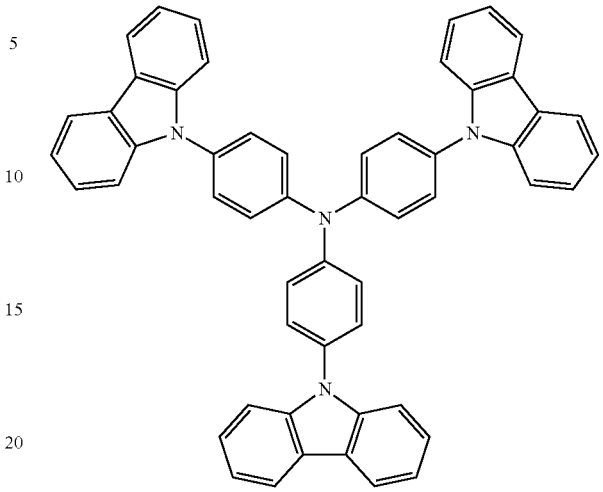

[chemical formula 1']

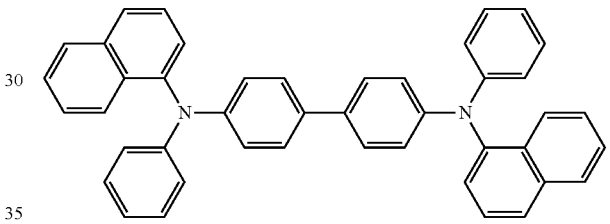

[chemical formula 2']

Recently, for effectively increasing the lighting performance of OLEDs, OLED manufactures and researchers have made great efforts to develop electron transport materials with hole blocking functionality, such as TmPyPb, TPBi, 3TPYMB, BmPyPb, and DPyPA represented by following chemical formula 3'-7', respectively. Wherein TmPyPb is the abbreviation of 3,3'-[5'-[3-(3-Pyridinyl)phenyl][1,1':3',1"-terphenyl]-3,3"-diyl]bispyridine, TPBi is the abbreviation of 1,3,5-Tris(1-phenyl-1H-benzimidazol-2-yl)benzene, 3TPYMB is the abbreviation of Tris(2,4,6-triMethyl-3-(pyridin-3-yl)phenyl)borane, BmPyPb is the abbreviation of 1,3-bis(3,5-dipyrid-3-yl-phenyl)benzene, and DPyPA is the abbreviation of 9,10-bis(3-(pyridin-3-yl)phenyl)anthracene.

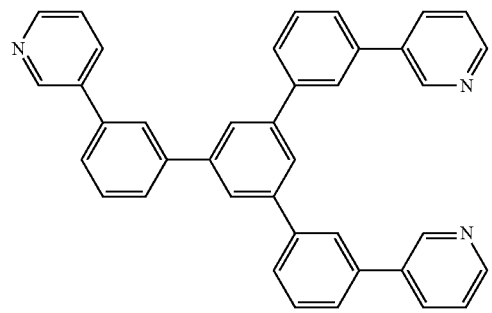

[chemical formula 3']

[chemical formula 4']

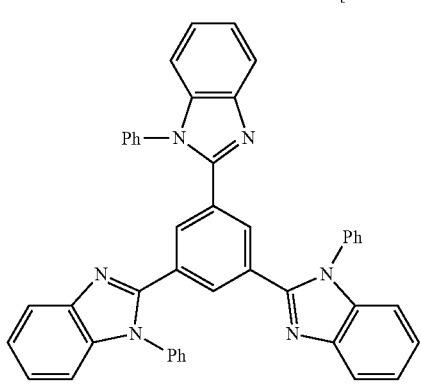

[chemical formula 5']

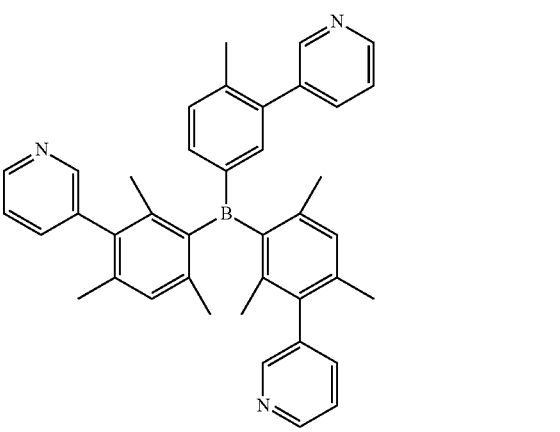

[chemical formula 6']

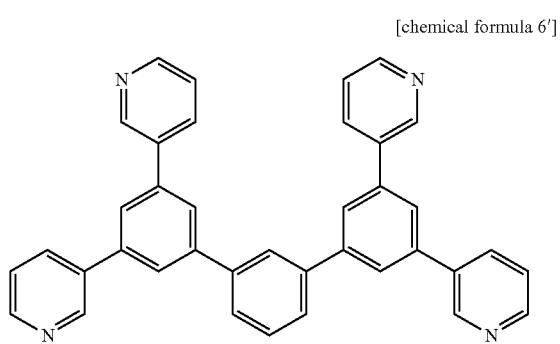 [SMILES: c1cncc(-c2cc(-c3cccnc3)cc(-c3cccc(-c4cc(-c5cccnc5)cc(-c5cccnc5)c4)c3)c2)c1]

[chemical formula 7']

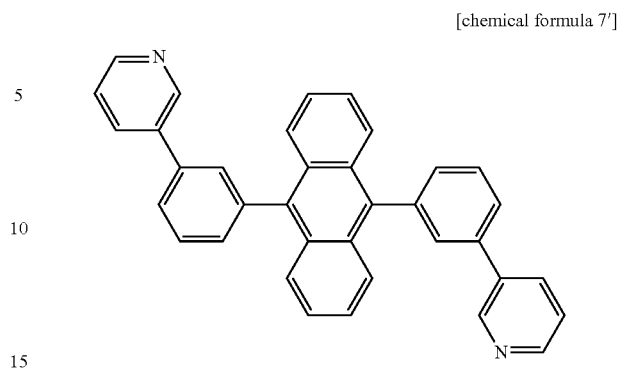

In spite of various electron transport materials with hole blocking functionality have been developed, the phosphorescence OLEDs applied with the said electron transport materials still cannot perform outstanding luminous efficiency and device lifetime. Accordingly, in view of the conventional or commercial electron transport materials with hole blocking functionality still including drawbacks, the inventor of the present application has made great efforts to make inventive research thereon and eventually provided a spirally configured cis-stilbene/fluorene hybrid material as hole-blocking type electron-transporter for OLED.

SUMMARY OF THE INVENTION

The primary objective of the present invention is to provide a spirally configured cis-stilbene/fluorene hybrid materials, which are spirally-configured cis-stilbene/fluorene derivatives having glass transition temperatures ranged from 110° C. to 135° C., decomposition temperatures ranged from 380° C. to 425° C., reversible electron transport property, and balanced charges motilities. In addition, a variety of experimental data have proved that this spirally configured cis-stilbene/fluorene hybrid materials can indeed be used as hole-blocking type electron-transporters and/or n-type host materials for OLEDs; moreover, the experimental data also reveal that the OLEDs using the spirally configured cis-stilbene/fluorene hybrid materials can indeed be used as the hole-blocking type electron-transporters and are able to show excellent external quantum efficiency ($\eta_{ext}$), current efficiency ($\eta_c$), power efficiency ($\eta_p$), maximum luminance ($L_{max}$), and device lifetime better than those of phosphorescent OLEDs based on the conventional or commercial electron transport materials.

Accordingly, in order to achieve the primary objective of the present invention, the inventor of the present invention provides a series of spirally configured cis-stilbene/fluorene hybrid materials for OLEDs, wherein the spirally configured cis-stilbene/fluorene hybrid materials are spirally-configured cis-stilbene/fluorene derivatives having the functions to block holes and constructed by at least one cis-Stilbene based component and at least one fluorene based component; moreover, the spirally configured cis-stilbene/fluorene hybrid materials can also applied to light-emitting host materials.

According to one embodiment of the spirally configured cis-stilbene/fluorene hybrid materials, wherein the said spirally-configured cis-stilbene/fluorene derivatives are represented by following chemical formula I:

[chemical formula I]

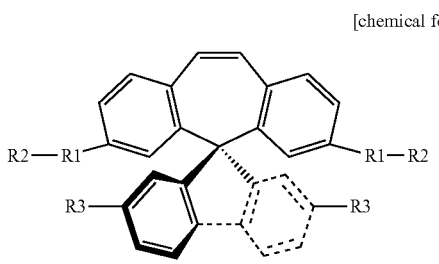

In the chemical formula I, R1-R2 are selected from the groups consisting of following chemical formula I-1, chemical formula I-2, chemical formula I-3, chemical formula I-4, chemical formula I-5a, chemical formula I-5b, chemical formula I-5c, chemical formula I-6a, chemical formula I-6b, and chemical formula I-6c:

[chemical formula I-1]

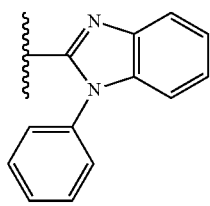

[chemical formula I-3]

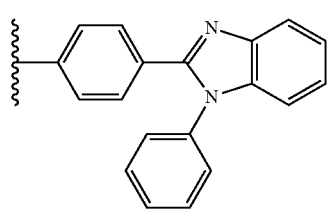

[chemical formula I-3]

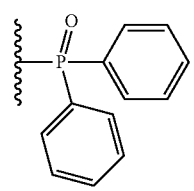

[chemical formula I-4]

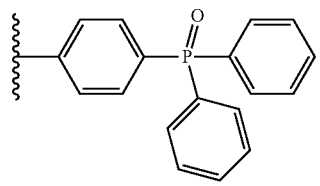

[chemical formula I-5a]

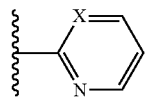

[chemical formula I-5b]

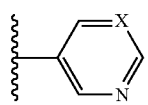

[chemical formula I-5c]

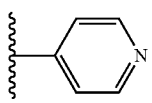

[chemical formula I-6a]

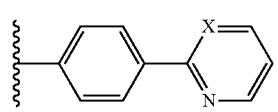

[chemical formula I-6b]

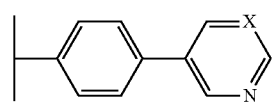

[chemical formula I-6c]

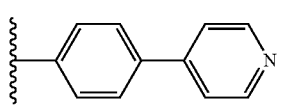

Wherein X in aforesaid chemical formula I-5a, chemical formula I-5b, chemical formula I-6a, and chemical formula I-6b is C—H group or N group, and R3 is selected from the group consisting of following chemical formula I-7 and chemical formula I-8:

—H   [chemical formula I-7]

[chemical formula I-8]

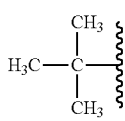

According to one embodiment of the spirally configured cis-stilbene/fluorene hybrid materials, wherein the spirally configured cis-stilbene/fluorene hybrid materials are represented by formula II, chemical formula III, chemical formula IV, chemical formula V, chemical formula VIa, chemical formula VIb, chemical formula VIc, chemical formula VIIa, chemical formula VIIb, and chemical formula VIIc:
[chemical formula II]
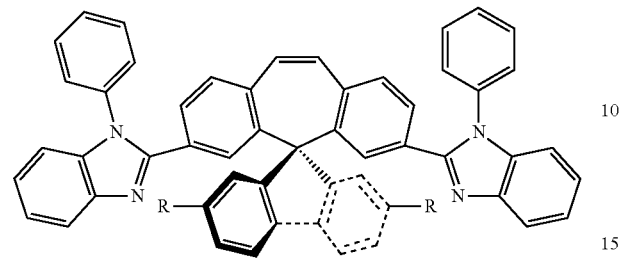
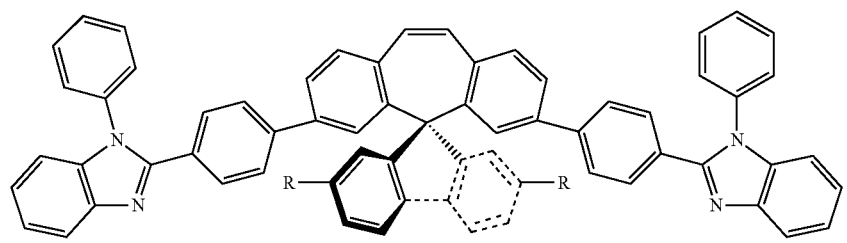
[chemical formula IV]
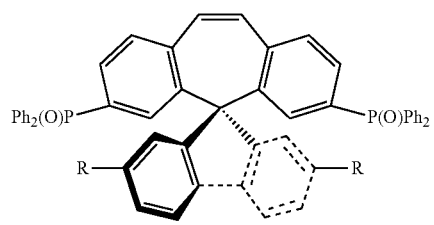
[chemical formula V]
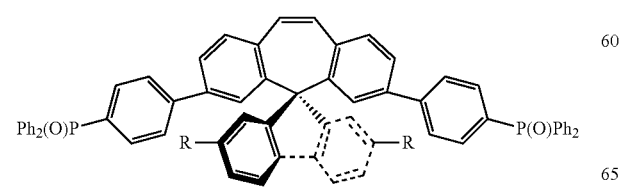
[chemical formula VIa]
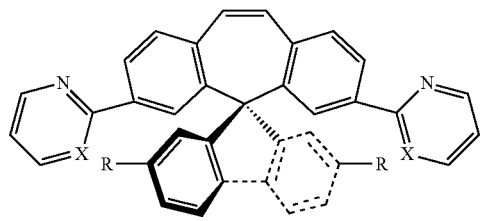
[chemical formula III]
[chemical formula VIb]
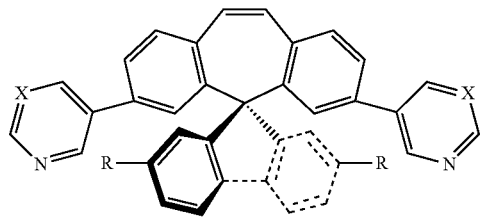
[chemical formula VIc]
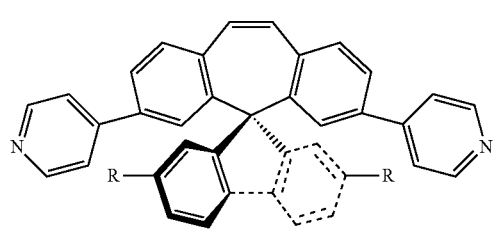

[chemical formula VIIa]

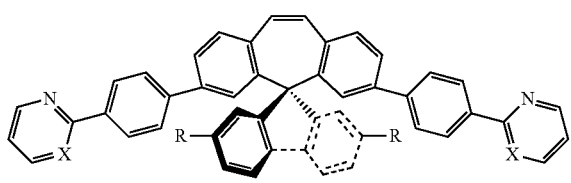

[chemical formula VIIb]

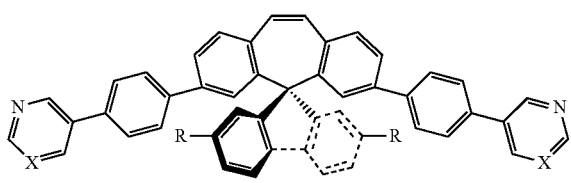

[chemical formula VIIc]

wherein R is hydrogen group or tert-butyl group, and X is C—H or N group.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

FIG. 1 is a framework view of a conventional organic light emitting diode (OLED).

DETAILED DESCRIPTION OF THE PREFERRED EMBODIMENTS

To more clearly describe spirally configured cis-stilbene/fluorene hybrid materials for OLEDs according to the present invention, embodiments of the present invention will be described in detail with reference to the attached drawings hereinafter.

The present invention provides a series of spirally configured cis-stilbene/fluorene hybrid materials for OLEDs. The spirally configured cis-stilbene/fluorene hybrid materials, constructed by at least one cis-Stilbene based component and at least one fluorene based component, are spirally-configured cis-stilbene/fluorene derivatives having the functions to block holes. These spirally configured cis-stilbene/fluorene hybrid materials are mainly applied in OLEDs for being as an electron transport layer and/or a hole blocking layer; moreover, these spirally configured cis-stilbene/fluorene hybrid materials can also be applied in a solar cell for being as a carrier transport layer.

In the present invention, the said spirally-configured cis-stilbene/fluorene derivatives are represented by following chemical formula I:

[chemical formula I]

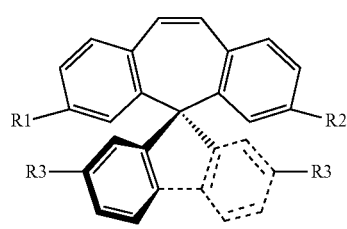

In the chemical formula I, R1-R2 is selected from the group consisting of following chemical formula I-1, chemical formula I-2, chemical formula I-3, chemical formula I-4, chemical formula I-5a, chemical formula I-5b, chemical formula I-5c, chemical formula I-6a, chemical formula I-6b, and chemical formula I-6c:

[chemical formula I-1]

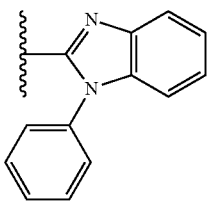

[chemical formula I-2]

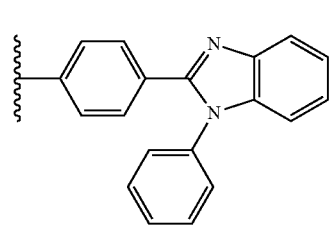

[chemical formula I-3]

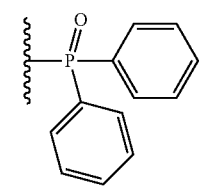

[chemical formula I-4]

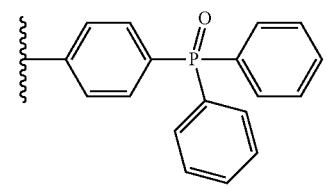

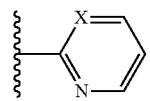 [chemical formula I-5a]

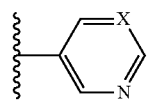 [chemical formula I-5b]

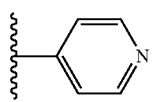 [chemical formula I-5c]

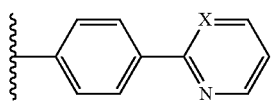 [chemical formula I-6a]

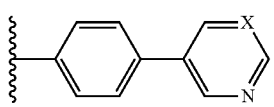 [chemical formula I-6b]

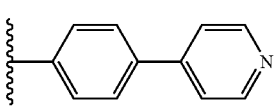 [chemical formula I-6c]

In the chemical formulas, X in aforesaid chemical formula I-5a, chemical formula I-5b, chemical formula I-6a, and chemical formula I-6b is C—H group or N group, and R3 is selected from the group consisting of following chemical formula I-7 and chemical formula I-8:

—H  [chemical formula I-7]

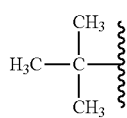 [chemical formula I-8]

To manufacture the said spirally configured cis-stilbene/fluorene hybrid materials of the present invention, a key intermediate product needs to be firstly fabricated by using following steps:

(1) dissolving 30 mM 2-bromobiphenyl of 5.2 mL in 100 mL of anhydrous tetrahydrofuran (THF);

(2) placing the solution obtained from the step (1) in an environment of −78° C. for standing;

(3) taking 12 mL of n-butyllithium in hexanes solution (30 mM) from a n-butyllithium solution 2.5 M in hexanes, and then adding the 12 mL n-butyllithium hexanes solution dropwise into the solution obtained from the step (2) and stirring for 30 min (4) dissolving 20 mM 3,7-dibromo-dibenzosuberenone of 7.28 g in 60 mL of anhydrous THF;

(5) adding the solution obtained from step (4) to the reaction mixture in step (3) dropwise;

(6) adding 10 mL of saturated aqueous sodium bicarbonate solution into the product obtained from the step (5) for executing a quenching reaction, and then remove the THF by rotary evaporation;

(7) treating the product obtained from the step (6) with a extracting process by using dichloromethane, and then obtaining an extract liquid extract;

(8) adding 5 g magnesium sulfate into the extract liquid extract, and then treat a drying process and a filtering process to the liquid extract sequentially; and (9) using a rotary evaporating process to the product obtained from the step (8), so as to obtain a an intermediate product. Furthermore, the following steps can be used for making another intermediate product of clear crystalline material.

(10) dissolving the intermediate product from step (9) in 60 m acetic acid;

(11) adding 1 mL of concentrated hydrochloric acid (12 N) into the solution obtained from the step (10);

(12) letting the solution mixture obtained from the step (11) to react for 2 hours at 120° C. by using a reflux device;

(13) cooling the temperature of the product obtained from the step (12) down to 0° C.;

(14) adding 60 mL hexane into the product obtained from the step (13);

(15) using a Buchner funnel to treat the product obtained from the step (14) with a filtering process, so as to obtain a precipitate;

(16) using hexane to wash the precipitate for 3 times, so as to obtain a solid material;

(17) using dichloromethane/hexane to treat the solid with a recrystallization process for obtaining a clear crystal solid, wherein the clear crystal solid is presented by following chemical formula 1.

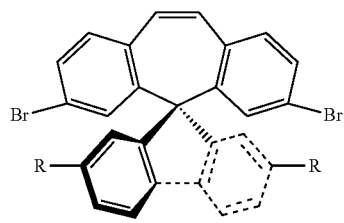 [chemical formula I]

Furthermore, various exemplary embodiments for the spirally configured cis-stilbene/fluorene hybrid materials of the present invention can be fabricated by treating certain chemical reaction method to the key intermediate product of clear crystalline materials represented by the chemical formula 1, such as Hartwig reaction and Rosemund-VonBarann method. Therefore, the exemplary embodiments 1-6 of the spirally configured cis-stilbene/fluorene hybrid materials are represented by following chemical formula II, chemical formula III, chemical formula IV, chemical formula V, chemical formula VI (comprising VIa, VIb and VIc), and chemical formula VII (comprising VIIa, VIIb and VIIc):
[chemical formula II]
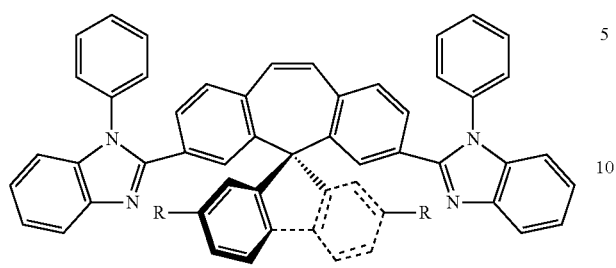
[chemical formula VIb]
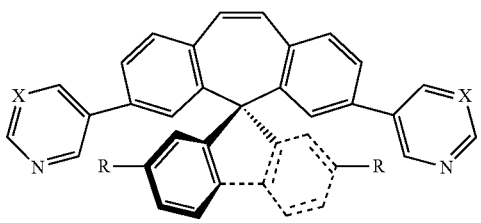
[chemical formula III]
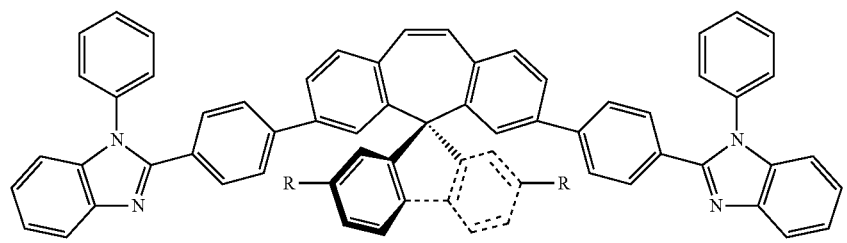
[chemical formula IV]
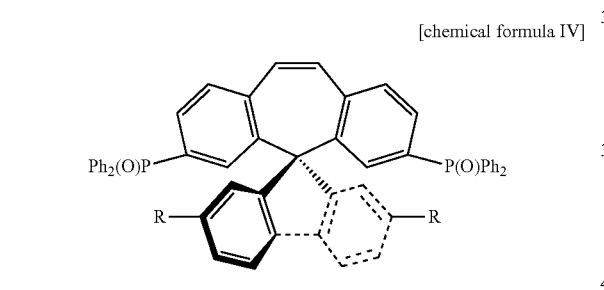
[chemical formula VIc]
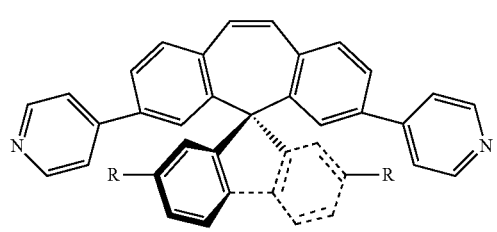
[chemical formula V]
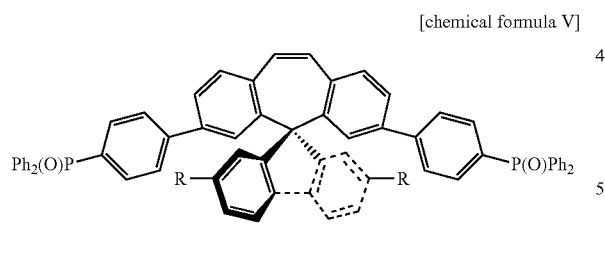
[chemical formula VIIa]
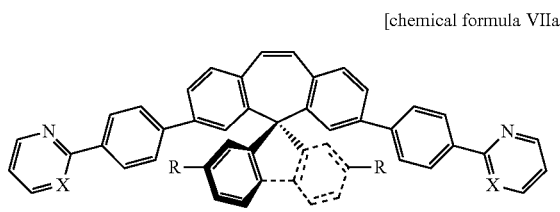
[chemical formula VIa]
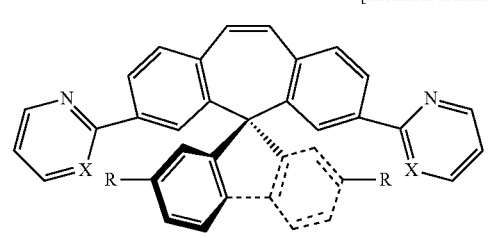
[chemical formula VIIb]
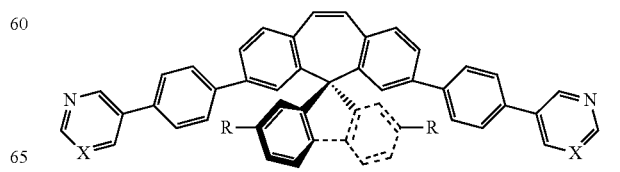

[chemical formula VIIc]

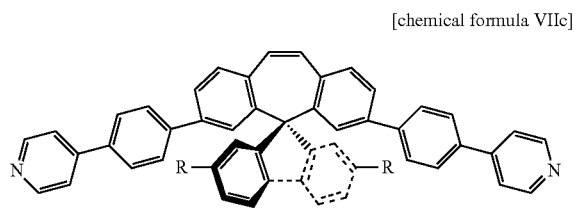

In the above-presented chemical formulas, R can be hydrogen group or tert-butyl group, and X is C—H or N group. Moreover, the data of glass transition temperature ($T_g$), decomposition temperature ($T_d$), the longest peak wavelength value of absorption spectrum ($\lambda_{max}$), and the longest peak wavelength value of photoluminescence spectrum (PL_$\lambda_{max}$) of the aforesaid embodiments 1-6 are measured and recorded in the following Table (1). From the Table (1), it is able to know that the spirally configured cis-stilbene/fluorene hybrid materials proposed by the present invention have glass transition temperatures ($T_g$) ranged from 113° C. to 135° C. and decomposition temperatures ($T_d$) ranged from 384° C. to 420° C. That means these spirally configured cis-stilbene/fluorene hybrid materials possess excellent thermal stability, and are not easy to decompose under high voltage and high current density operation conditions.

TABLE (1)

| Group | $T_g$ (° C.) | $T_d$ (° C.) | $\lambda_{max}$ (nm) | PL$\lambda_{max}$ (nm) |
|---|---|---|---|---|
| Embodiment 1 (BSB) | 125 | 403 | 366 | 431 |
| Embodiment 2 (BΦSΦB) | 135 | 420 | 356 | 435 |
| Embodiment 3 (PSP) | 113 | 384 | 334 | 386 |
| Embodiment 4 (PΦSΦP) | 127 | 398 | 328 | 390 |
| Embodiment 5 (PySPy) | 115-122 | 400-411 | 365-368 | 415-419 |
| Embodiment 6 (PyΦSΦPy) | 123-131 | 412-419 | 380-385 | 421-425 |

Moreover, the oxidation potential and the redox potential of the embodiments 1-6 of the spirally configured cis-stilbene/fluorene hybrid materials can be measured by way of cyclic voltammetry (CV); therefore, the highest occupied molecular orbital energy level ($E_{HOMO}$) and lowest unoccupied molecular orbital energy level ($E_{LUMO}$) of the embodiments 1-6 of the spirally configured cis-stilbene/fluorene hybrid materials can also be calculated based on the measured oxidation potential ($E_{1/2}^{ox}$) and the redox potential ($E_{1/2}^{red}$). With reference to following Table (2), $E_{1/2}^{ox}$, $E_{1/2}^{red}$, $E_{HOMO}$, and $E_{LUMO}$ of the spirally configured cis-stilbene/fluorene hybrid materials are recorded. From the Table (2), the persons skilled in OLED material art are able to know that the spirally configured cis-stilbene/fluorene hybrid materials proposed by the present invention have the $E_{HOMO}$ ranged from 5.61 eV to 6.0 eV and the $E_{LUMO}$ ranged from 2.63 eV to 3.0 eV. Moreover, the spirally configured cis-stilbene/fluorene hybrid materials also have the oxidation potentials ranged from 0.81 V to 1.07 V and the redox potentials ranged from −1.65 V to −2.27 V.

TABLE (2)

| Group | $E_{1/2}^{ox}$ (V) | $E_{1/2}^{red}$ (V) | Eg (eV) | $E_{HOMO}$ (eV) | $E_{LUMO}$ (eV) |
|---|---|---|---|---|---|
| Embodiment 1 (BSB) | 0.93 | −2.27 | 3.00 | 6.0 | 3.0 |
| Embodiment 2 (BΦSΦB) | 0.87 | −2.24 | 3.00 | 5.7 | 2.7 |
| Embodiment 3 (PSP) | 1.07 | −1.73 | 3.24 | 5.87 | 2.63 |
| Embodiment 4 (PΦSΦP) | 1.07 | −1.65 | 3.20 | 5.87 | 2.67 |
| Embodiment 5 (PySPy) | 0.84-0.87 | −1.9~−1.98 | 2.91-2.94 | 5.64-5.67 | 2.73-2.76 |
| Embodiment 6 (PyΦSΦPy) | 0.81-0.84 | −1.91~−1.95 | 2.96-2.98 | 5.61-5.63 | 2.63-2.67 |

In order to prove that the proposed spirally configured cis-stilbene/fluorene hybrid materials can indeed be applied in OLEDs for being as a hole-blocking type electron transport layer, a plurality of OLED devices for control groups and experiment groups have been designed and manufactured, wherein the constituting layers for the OLED devices are integrated in the following Table (3).

TABLE 3

| Device Group | substrate | bottom electrode | electron transport layer | hole blocking layer | Light emitting layer | Hole transport layer | top electrode |
|---|---|---|---|---|---|---|---|
| Experiment 1a | Al | LiF | BSB | BSB | green phosphorescent | TAPC | HIL/ITO |
| Experiment 1b | Al | LiF | BΦSΦB | BΦSΦB | green phosphorescent | TAPC | HIL/ITO |
| Experiment 2a | Al | LiF | PSP | PSP | green phosphorescent | TAPC | HIL/ITO |
| Experiment 2b | Al | LiF | PΦSΦP | PΦSΦP | green phosphorescent | TAPC | HIL/ITO |
| Experiment 3a | Al | LiF | PySPy | PySPy | green phosphorescent | TAPC | HIL/ITO |
| Experiment 3b | Al | LiF | PyΦSΦPy | PyΦSΦPy | green phosphorescent | TAPC | HIL/ITO |

TABLE 3-continued

| Device Group | substrate | bottom electrode | electron transport layer | hole blocking layer | Light emitting layer | Hole transport layer | top electrode |
|---|---|---|---|---|---|---|---|
| Control 1A | Al | LiF | BmPyPb | BmPyPb | green phosphorescent | TAPC | HIL/ITO |
| Control 1B | Al | LiF | DPyPA | DPyPA | green phosphorescent | TAPC | HIL/ITO |
| Control 1C | Al | LiF | TPBi | TPBi | green phosphorescent | TAPC | HIL/ITO |
| Control 1D | Al | LiF | Alq3 | Alq3 | green phosphorescent | TAPC | HIL/ITO |
| Experiment 4 | Al | LiF | BSB | BSB | green phosphorescent | NPB/HT01 | HIL/ITO |
| Experiment 5 | Al | LiF | PΦSΦP | PΦSΦP | green phosphorescent | NPB/HT01 | HIL/ITO |
| Control 2 | Al | LiF | BmPyPb | BmPyPb | green phosphorescent | NPB/HT01 | HIL/ITO |
| Control 3 | Al | LiF | ET01 | ET01 | green phosphorescent | NPB/HT01 | HIL/ITO |

In the Table (3), BmPyPb is the abbreviation of 1,3-bis(3,5-dipyrid-3-yl-phenyl)benzene, DPyPA is the abbreviation of 9,10-bis(3-(pyridin-3-yl)phenyl)anthracene, TPBi is the abbreviation of 1,3,5-Tris(1-phenyl-1H-benzimidazol-2-yl)benzene, and $Alq_3$ is the abbreviation of tris(8-hydroxyquinoline) aluminium(iii). In addition, ET01 is represented by following chemical formula 2''.

[chemical formula 2'']

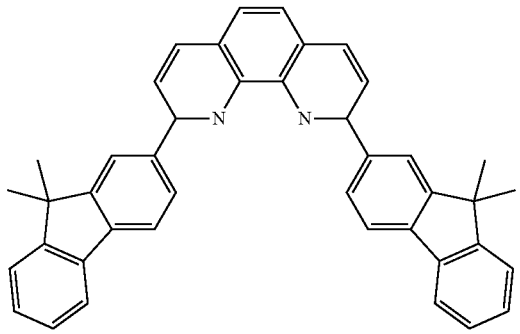

It is able to know that the materials of $Alq_3$, TPBi, BmPyPb, and ET01 recorded in the Table (3) are also used as OLED device's electron transport layers. Continuously, the turn-on voltage ($V_{on}$), the external quantum efficiency ($\eta_{ext}$), the current efficiency ($\eta_c$), the power efficiency ($\eta_p$), and the maximum luminance ($L_{max}$) of the OLED devices have been measured and recorded in the following Table (4).

TABLE (4)

| Device Group | $\lambda_{max}$ (nm) | Von (V) | $\eta_{ext}$ (%) | $\eta_c/\eta_p$ (%) | $L_{max}$ (cd/m$_2$) |
|---|---|---|---|---|---|
| Experiment 1a | 516 | 4.9 | 15.6 | 54.4/34.9 | 103740 |
| Experiment 1b | 516 | 4.9 | 15.0 | 52.2/31.7 | 90735 |
| Experiment 2a | 516 | 2.5 | 11.0 | 38.0/28.6 | 116900 |
| Experiment 2b | 516 | 2.1 | 16.7 | 58.7/43.9 | 193800 |
| Experiment 3a | 516 | 3.0 | 16.0 | 53.6/33.6 | 128500 |
| Experiment 3b | 516 | 2.3 | 10.5 | 35.5/26.4 | 105840 |
| Control 1A | 516 | 2.5 | 6.3 | 22.8/18.0 | 142100 |
| Control 1B | 516 | 3.0 | 10.2 | 37.8/24.0 | 40700 |
| Control 1C | 516 | 3.0 | 6.9 | 24.7/22.0 | 37640 |
| Control 1D | 516 | 2.8 | 3.4 | 11.5/9.7 | 42140 |
| Experiment 4 | 516 | 5.5 | 10.6 | 35.9/20.5 | 24350 |
| Experiment 5 | 516 | 5.0 | 11.9 | 40.7/25.6 | 40000 |
| Control 2 | 516 | 4.5 | 10.8 | 36.8/25.7 | 42150 |
| Control 3 | 516 | 5.5 | 7.84 | 27.6/15.8 | 17700 |

With reference to the measured data of the green phosphorescent OLED devices in the Table (4), one can find that the OLED devices using single hole transport layer of Experiment 1a-b, Experiment 2a-b and experiment 3a-b show excellent $\eta_{ext}$, $\eta_c$, $\eta_p$, and $L_{max}$ and are much superior to the OLED devices using single hole transport layer of Control 1A, Control 1B, Control 1C, and Control 1D. Among them, experiments 1a (BSB), 2b (PΦSΦP), and 3a (PySPy) show the best results, where the $\eta_{ext}$ are in a range of 15.6-16.7%, $\eta_c$ are in a range of 53.6-58.7 cd/A, $\eta_p$ are in a range of 33.6-43.9 lm/w, and $L_{max}$ are in a range of 103740-193800 cd/m$^2$.

In addition, the measured data also reveal that the OLED devices using single hole transport layer of Experiment 1a-b, Experiment 2a-b, and Experiment 3a-b show excellent $\eta_{ext}$, $\eta_c$, $\eta_p$, and $L_{max}$ and are superior to the OLED devices using complex (i.e., double) hole transport layer of Control 1, Control 2 and Control 3. Moreover, the commercial OLED device using complex (double) hole transport layer of Experiment 5 (PΦSΦP) also shows excellent $\eta_{ext}$, $\eta_c$, $\eta_p$, and $L_{max}$, which is superior to the OLED devices using complex (i.e., double) hole transport layer of Control 1, Control 2 and Control 3.

Furthermore, device life time evaluation test for the green phosphorescent OLEDs have also been completed based on a starting luminance of 10000 cd/cm². Life time evaluation test results reveal that the decay half lifetime ($LT_{50}$) of the green phosphorescent OLED of Experiment 2a is 14,000 hours. In addition, the decay half lifetime ($LT_{50}$) for the green phosphorescent OLEDs of Control 1A and Control 3 are respectively measured as 1,000 hours and 20,000 hours. Moreover, after replacing the BmPyPb in the green phosphorescent OLEDs of Control 1A by the TmPyPb, the green phosphorescent OLEDs having the TmPyPb material is measured with the $LT_{50}$ of only 210 hours.

In order to prove that the proposed spirally configured cis-stilbene/fluorene hybrid materials can indeed be applied in OLEDs for being as a n-type, host material in an phosphorescent red emitting layer, several of OLED devices for a control group and experiment groups have been designed and manufactured, wherein the constituting layers for the OLED devices are integrated in the following Table (5).

TABLE 5

| Device Group | substrate | bottom electrode | electron transport layer | hole blocking layer | Host material | Light emitting layer | Hole transport layer | top electrode |
|---|---|---|---|---|---|---|---|---|
| Expt. 1a | Al | LiF | BSB | 3TPYMB | PSP | Red | TAPC | HIL/ITO |
| Expt. 1b | Al | LiF | BSB | 3TPYMB | PΦSΦP | Red | TAPC | HIL/ITO |
| Control 1 | Al | LiF | BΦSΦB | TPBi | CBP | Red | TAPC | HIL/ITO |

With reference to the measured data of the red phosphorescent OLED devices in the Table (6), one can find that the OLED devices using single hole transport layer of Experiment 1a-b and 3TPYMB (represented by following chemical formula 3″) as the hole blocking layer show excellent $\eta_{ext}$, $\eta_c$, $\eta_p$, and $L_{max}$ and are better than the OLED device using single hole transport layer of Control 1 and TPBi as the hole blocking layer. Among them, experiments 1a (PSP), and 1b (PΦSΦP) show the best results, where the $\eta_{ext}$ are in a range of 16.0-16.9%, $\eta_c$ are in a range of 22.2-25.7 cd/A, $\eta_p$ are in a range of 23.3-25.4 lm/w, and $L_{max}$ are in a range of 29600-30520 cd/m². These results are based on a red phoisphorescent device configuration: ITO/PEDOT:PSS/NPB (20 nm)/TCTA (5 nm)/10% Ir(piq)3 or OS1(25 nm)/3TPYMB (50 nm)/LiF/Al, with an emission $\lambda_{max}$ of 616 nm and fwhm=76 nm; CIE(x,y)=(0.63, 0.36). The overall current and power efficiencies are improved by 48% and 78%, respectively. Wherein the material OS1 is represented by following chemical formula 4″.

[chemical formula 3″]

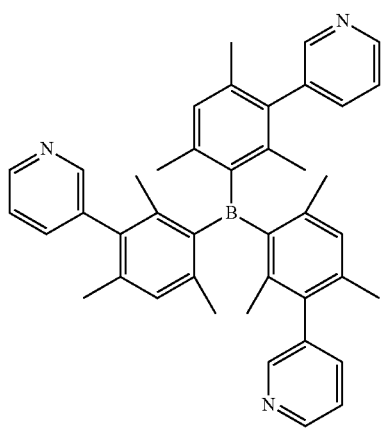

[chemical formula 4″]

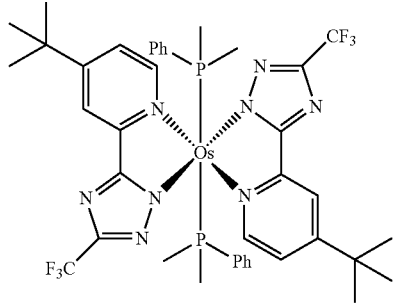

TABLE (6)

| Device Group | $\lambda_{max}$ (nm) | Von (V) | $\eta_{ext}$ (%) | $\eta_c/\eta_p$ (%) | $L_{max}$ (cd/m₂) |
|---|---|---|---|---|---|
| Experiment 1a | 616 | 2.5 | 16.0 | 22.2/23.3 | 29600 |
| Experiment 1b | 616 | 2.4 | 16.9 | 25.7/25.4 | 30520 |
| Control 1 | 616 | 3.4 | 16.1 | 15.8/12.2 | 5820 |

Therefore, through above descriptions, the spirally configured cis-stilbene/fluorene hybrid materials for OLEDs proposed by the present invention have been introduced completely and clearly; in summary, the present invention includes the advantages of:

(1) The spirally configured cis-stilbene/fluorene hybrid materials are spirally-configured cis-stilbene/fluorene derivatives having glass transition temperatures ranged from 110° C. to 135° C., decomposition temperatures ranged from 380° C. to 425° C., reversible electron transport property, and balanced charges motilities.

(2) Moreover, a variety of experimental data have proved that this spirally configured cis-stilbene/fluorene hybrid materials can indeed be used as a hole-blocking type electron-transporter and/or a host material for OLEDs; moreover, the experiment data also reveal that the OLEDs using the spirally configured cis-stilbene/fluorene hybrid materials can indeed be used as the hole-blocking type electron-transporter are able to show excellent external quantum efficiency ($\eta_{ext}$), current efficiency ($\eta_c$), power efficiency ($\eta_p$), maximum luminance ($L_{max}$), and device lifetime performances better than the conventional or commercial OLEDs.

The above description is made on embodiments of the present invention. However, the embodiments are not intended to limit scope of the present invention, and all equivalent implementations or alterations within the spirit of the present invention still fall within the scope of the present invention.

What is claimed is:

1. A spirally configured cis-stilbene/fluorene hybrid material capable of being applied in an organic light emitting diode (OLED) for being as an electron transport layer and/or a hole blocking layer, wherein the spirally configured cis-stilbene/fluorene hybrid material is represented by following chemical formulas II, III, IV, V, VI, or VII:

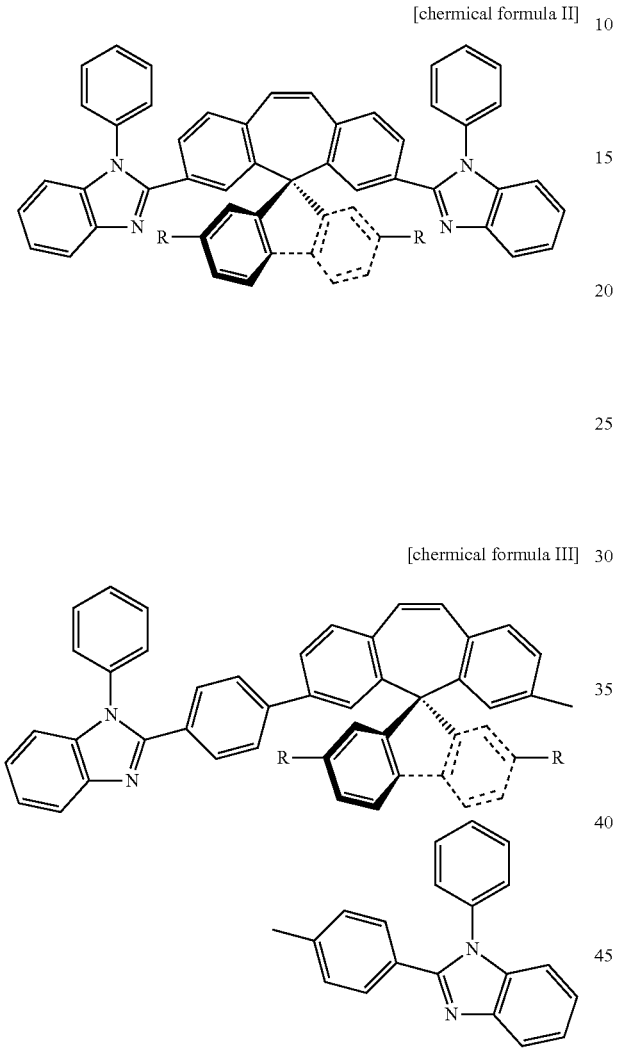

[chemical formula II]

[chemical formula III]

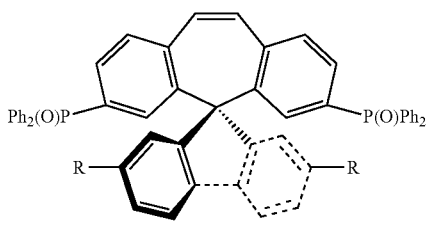

[chemical formula IV]

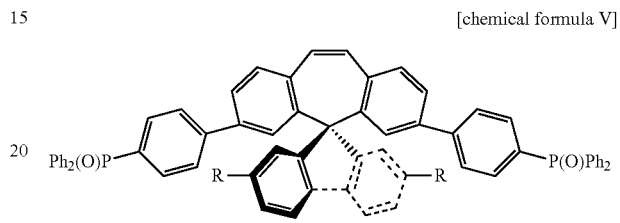

[chemical formula V]

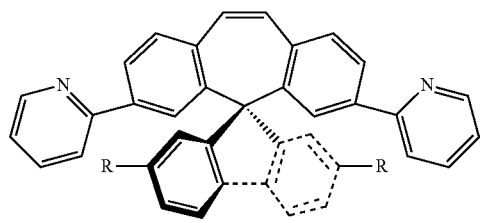

[chemical formula VI]

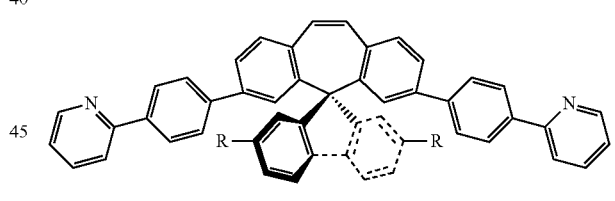

[chemical formula VII]

wherein R in chemical formulas II-VII is tert-butyl group.

* * * * *